United States Patent
Ouyang

(10) Patent No.: US 11,470,880 B2
(45) Date of Patent: Oct. 18, 2022

(54) ATOMIZER AND ELECTRONIC CIGARETTE HAVING SAME

(71) Applicant: SHENZHEN IVPS TECHNOLOGY CO., LTD., Shenzhen (CN)

(72) Inventor: Junwei Ouyang, Shenzhen (CN)

(73) Assignee: SHENZHEN IVPS TECHNOLOGY CO., LTD., Shenzhen (CN)

( * ) Notice: Subject to any disclaimer, the term of this patent is extended or adjusted under 35 U.S.C. 154(b) by 445 days.

(21) Appl. No.: 16/508,313

(22) Filed: Jul. 11, 2019

(65) Prior Publication Data

US 2020/0015523 A1    Jan. 16, 2020

(30) Foreign Application Priority Data

Jul. 11, 2018  (CN) .......................... 201821120112.0

(51) Int. Cl.
| | |
|---|---|
| *A24F 47/00* | (2020.01) |
| *A24F 40/40* | (2020.01) |
| *A61M 11/04* | (2006.01) |
| *A24F 40/10* | (2020.01) |

(52) U.S. Cl.
CPC ........... *A24F 40/40* (2020.01); *A61M 11/042* (2014.02); *A24F 40/10* (2020.01); *A61M 2205/8206* (2013.01)

(58) Field of Classification Search
CPC .............................. A61M 11/042; A24F 40/40
See application file for complete search history.

(56) References Cited

U.S. PATENT DOCUMENTS

| | | | | | |
|---|---|---|---|---|---|
| 4,242,719 | A | * | 12/1980 | Conley | H05K 3/328 174/262 |
| 5,564,442 | A | * | 10/1996 | MacDonald | A24F 40/40 131/194 |
| 9,220,302 | B2 | * | 12/2015 | DePiano | A24F 40/42 |
| 9,820,509 | B2 | * | 11/2017 | Newton | A24F 40/60 |
| 9,913,494 | B2 | * | 3/2018 | Liu | A24F 40/50 |
| 10,058,130 | B2 | * | 8/2018 | Monsees | A24F 7/00 |
| 10,213,611 | B2 | * | 2/2019 | Kim | A61N 1/375 |
| 10,375,997 | B2 | * | 8/2019 | Guo | A24F 40/44 |
| 11,031,798 | B2 | * | 6/2021 | Sun | A24F 1/00 |

(Continued)

FOREIGN PATENT DOCUMENTS

| | | |
|---|---|---|
| CN | 107890142 A | 4/2018 |
| WO | 2016090593 A1 | 6/2016 |
| WO | 2017163045 A1 | 9/2017 |

*Primary Examiner* — Neil Abrams
(74) *Attorney, Agent, or Firm* — IP-PAL Patent US

(57) ABSTRACT

The present invention discloses an atomizer and an electronic cigarette, wherein the atomizer comprises a main body, the main body is provided with an atomizing assembly and two conductive terminals, the two conductive terminals are electrically connected with the atomizing assembly at one end, and are electrically connected with the external power supply at the other end, the main body is further provided with two conducting strips, the two conducting strips are electrically connected with the two conductive terminals, respectively, and can be both electrically connected with the external power supply. The present invention increases the area of contact of the atomizer with the conductive position of the external power supply by providing conducting strips, thereby enhancing the stability of the current supplied by the atomizer.

16 Claims, 4 Drawing Sheets

(56) References Cited

U.S. PATENT DOCUMENTS

2019/0191765 A1* 6/2019 Chen .................. H01M 50/213
2020/0015523 A1* 1/2020 Ouyang ................ A61M 15/06
2020/0305502 A1* 10/2020 Ouyang ................. A24F 47/00

* cited by examiner

ATOMIZER AND ELECTRONIC CIGARETTE HAVING SAME

TECHNICAL FIELD

The present invention relates to an atomizer and an electronic cigarette.

BACKGROUND

Electronic cigarettes, also known as e-cigarettes, are mainly used to quit smoking and replace conventional cigarettes. It has an appearance and taste similar to conventional cigarettes, and even has more tastes than conventional cigarettes. It can generate smoke, a taste and a feel like conventional cigarettes. Since electronic cigarettes have no tar, suspension particles and other harmful components in conventional cigarettes and are popular among consumers, electronic cigarettes have gradually replaced conventional cigarettes in the market.

However, the existing atomizer typically forms a point contact between the conductive terminals and the output electrodes on the power supply assembly to form an electrical connection, so as to provide power. Such a point contact is too small, so that the supply current is unstable, and even the contact is poor, resulting in unstable operation of the atomizer.

SUMMARY

The main object of the present invention is to provide an atomizer and an electronic cigarette, which can improve the stability of the supply current by increasing the contact area of the conductive portion of the atomizer.

In order to achieve the above object, the present invention uses the following technical solutions:

an atomizer, comprising a main body, wherein the main body is provided with an atomizing assembly and two conductive terminals, the two conductive terminals are electrically connected with the atomizing assembly at one end, and are electrically connected with an external power supply at the other end; the main body is further provided with two conductive strips, and the two conductive strips are electrically connected with the two conductive terminals, respectively, and are both capable of being electrically connected with the external power supply.

According to the atomizer, the conductive terminal comprises a contact portion and a connecting portion, one end of the connecting portion is connected with the contact portion, the other end is electrically connected with the atomizing assembly; the conductive strip is provided with a first through hole and is sleeved at the connecting portion through the first through hole, and is fit to the contact portion.

According to the atomizer, the conductive strip is provided with an avoidance groove, the first through hole is located at the bottom wall of the avoidance groove, the connecting portion passes through the first through hole and is electrically connected with the atomizing assembly, and the contact portion is placed in the avoidance groove.

According to the atomizer, the depth of the avoidance groove is equal to the thickness of the contact portion.

According to the atomizer, the main body comprises a base and a housing, the base is provided with a receiving groove at one end, and covers the housing at the other end and forms a receiving chamber with the housing, the atomizing assembly is connected with the base and placed in the receiving chamber; the bottom wall of the receiving groove is provided with a second through hole concentric with the first through hole, the conductive strip is placed in the receiving groove, and the conductive terminal passes through the first through hole and the second through hole sequentially and is electrically connected with the atomizing assembly.

According to the atomizer, the bottom wall of the receiving groove is further provided with an air inlet, the two conductive strips are located at both sides of the air inlet, respectively, and the atomizing assembly is provided with an air flow passage communicated with the air inlet.

According to the atomizer, the outer wall of the connecting portion is provided with at least one oil-sealing rim at intervals circumferentially, and the oil-sealing rim is abutted against the inner wall of the second through hole.

According to the atomizer, the oil-sealing rim has a truncated cone shape, and the diameter of the oil-sealing rim decreases in a direction away from the contact portion.

According to the atomizer, the atomizing assembly comprises a mounting base, an oil guiding core mounted on the mounting base, and a heating wire wound around the oil guiding core; one end of the two conductive terminals away from the conductive strip is provided with a socket, one end of the heating wire is placed in the socket of one conductive terminal, the other end is placed in the socket of the other conductive terminal, and both ends of the heating wire are abutted against the inner wall of the corresponding socket.

An electronic cigarette comprises a battery assembly, further comprising an atomizer as described above, wherein the atomizer is electrically connected with the battery assembly through the conductive terminal and/or the conductive strip.

Beneficial Effects: Compared with the prior art, the present invention provides an atomizer and an electronic cigarette, wherein the atomizer comprises a main body, the main body is provided with an atomizing assembly and two conductive terminals, the two conductive terminals are electrically connected with the atomizing assembly at one end, and are provided with conducting strips at the other end, and the conducting strips are electrically connected with an external power supply through the two conductive terminals and/or the conducting strip, to supply power to the atomizing assembly so as to pass through the conductive terminal in the atomizer. The present invention increases the conductive contact area by providing a conductive strip at one end of the conductive terminal in contact with the external power supply, thereby enhancing the stability of the power supply current.

BRIEF DESCRIPTION OF THE DRAWINGS

For a better illustration of the embodiments of the present invention or the technical solution in the prior art, accompanying drawings needed in the description of the embodiments or the prior art are simply illustrated below. Obviously, the accompanying drawings described below are some embodiments of the present invention. For those skilled in the art, other accompanying drawings may be obtained according to the structure shown in these accompanying drawings without creative work.

DESCRIPTION OF THE REFERENCE NUMBERS

Figure 1:
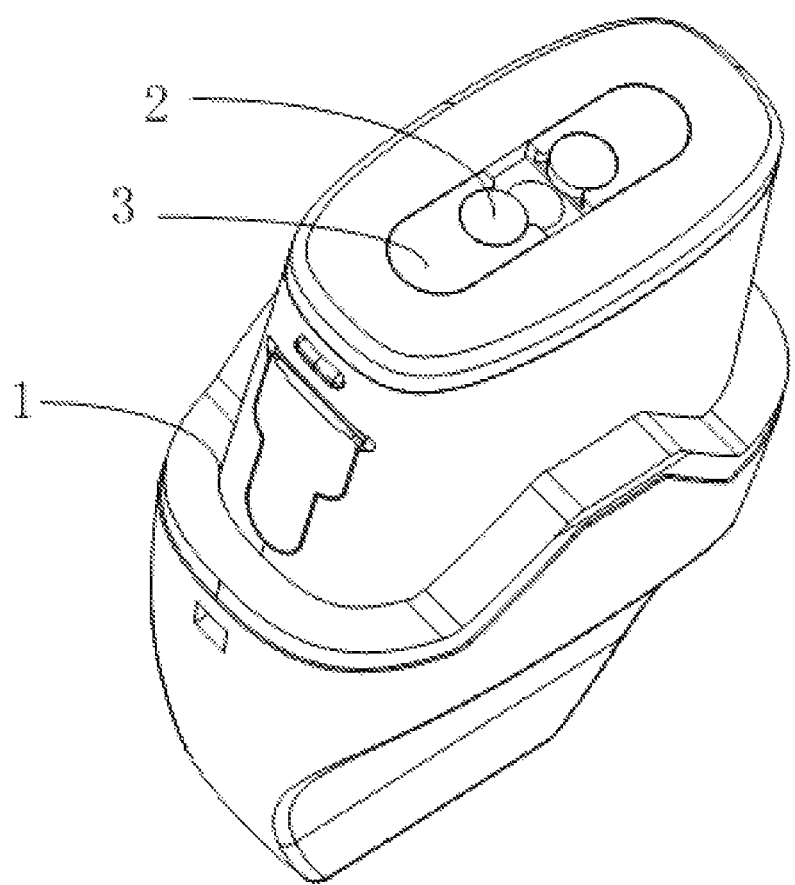
FIG. 1 is a schematic diagram illustrating a structure of an atomizer according to the present invention.

| Reference number | Name of part | Reference number | Name of part |
|---|---|---|---|
| 1 | main body | 2 | conductive terminal |
| 3 | conductive strip | 11 | base |
| 12 | housing | 13 | mounting base |
| 14 | oil guiding core | 21 | contact portion |
| 22 | connecting portion | 221 | oil-sealing rim |
| 222 | socket | 31 | first through hole |
| 32 | avoidance groove | 111 | receiving groove |
| 112 | air inlet | 113 | second through hole |

The implementation of aims, the function features and the advantages of the present disclosure are described below in further detail in conjunction with embodiments with reference to the drawings.

DESCRIPTION OF THE EMBODIMENTS

A clear and complete description as below is provided for the technical solution in the embodiments of the present invention in conjunction with the drawings in the embodiments of the present invention. Obviously, the embodiments described hereafter are simply part embodiments of the present invention, rather than all the embodiments. All other embodiments obtained by those skilled in the art based on the embodiments in the present invention without creative work are intended to be included in the scope of protection of the present invention.

It should be noted that all directional indications (such as top, bottom, left, right, front, behind . . . ) in the embodiments of the present invention are merely to illustrate a relative position relation, a relative motion condition, etc. between each part in a certain state (as shown in the drawings). If the state changes, the directional indication changes accordingly.

In addition, if terms "first", "second", etc. appear in the present invention, they are merely for the purpose of description, but cannot be understood as the indication or implication of relative importance or as the implicit indication of the number of the designated technical features; therefore, features defined by "first" and "second" may specifically or implicitly comprise at least one such feature. In addition, technical solutions of each embodiment of the present invention may be combined mutually; however, this must be carried out on the basis that those skilled in the art can implement the combination. When the combination of technical solutions has a conflict or cannot be implemented, it should be considered that such combination of technical solutions does not exist and is not in the scope of protection claimed by the present invention.

In the present invention, unless otherwise specifically stated and defined, terms "connected", "fixed", etc. should be interpreted expansively. For example, "fixed" may be fixed connection, detachable connection, or integration; may be mechanical connection or electrical connection; direct connection, indirect connection through an intermediate, or internal communication between two elements or interaction of two elements, unless otherwise specifically defined.

Those skilled in the art can understand the specific implication of the above terms in the present invention according to specific conditions.

The present invention provides an atomizer and an electronic cigarette. The atomizer comprises a main body 1, wherein the main body 1 is provided with an atomizing assembly (not shown) and two conductive terminals 2, the two conductive terminals 2 are electrically connected with the atomizing assembly at one end, and are electrically connected with an external power supply at the other end. The main body 1 is further provided with two conductive strips 3, and the two conductive strips 3 are electrically connected with the two conductive terminals 2, respectively, and are both capable of being electrically connected with the external power supply. In the present embodiment, by providing the conductive strips 3, the atomizing assembly can be electrically connected with the external power supply through the two conductive terminals 2 and/or the two conductive strips 3 to increase the area of contact of the atomizing assembly with the output electrode of the external power supply, thereby enhancing the stability of the supply current and improving the operational stability of the atomizer.

Figure 2:
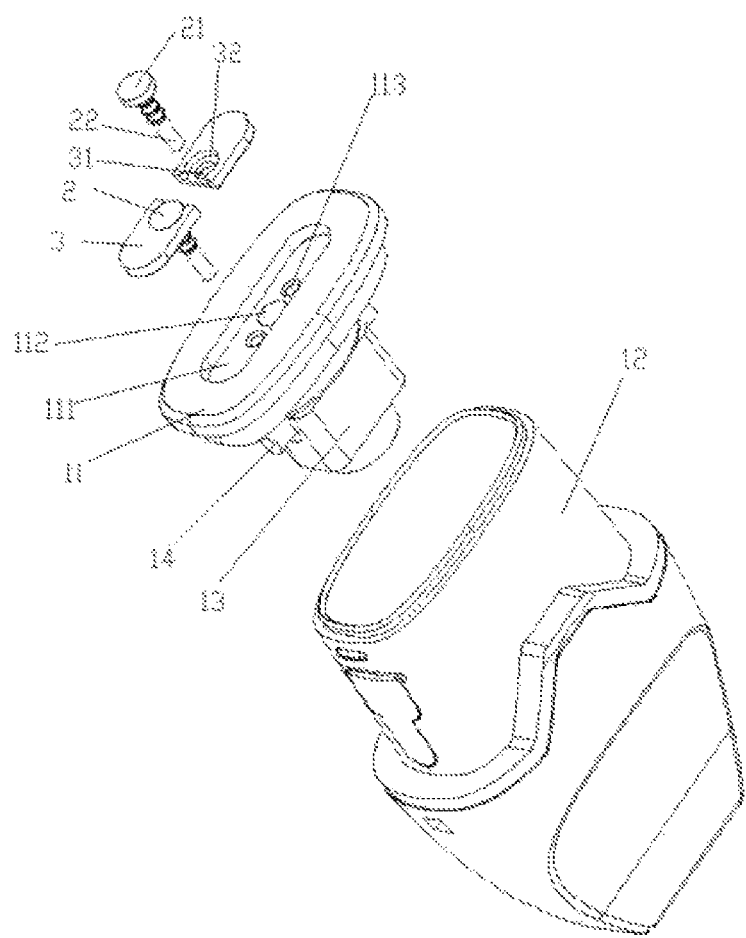
FIG. 2 is an exploded diagram illustrating an atomizer according to the present invention.

As shown in FIGS. 1 and 2, the conductive terminal 2 comprises a contact portion 21 and a connecting portion 22, one end of the connecting portion 22 is connected with the contact portion 21, and the other end is electrically connected with the atomizing assembly. The contact portion 21 and the connecting portion 22 may be integrally formed or may be detachably connected. The connecting portion 22 is of a columnar or strip-like structure. Preferably, the connecting portion 22 is a cylinder, and the contact portion 21 is of a disc type. Since the contact portion 21 is in contact with the output electrode of the external power supply, the diameter thereof is larger than the diameter of the connecting portion 22, thereby facilitating increasing the contact area. Of course, the connecting portion 22 and the contact portion 21 may be, but are not limited to, the above structure, and may be made of other shapes and structures made of a conductive material. In the embodiment, the conductive strip 3 is provided with a first through hole 31, the connecting portion 22 passes through the first through hole, and the contact portion 21 is fit to the conductive strip 3, ensuring that the conductive strip 3 is electrically connected with the conductive terminal 2, so that the current introduced from the conductive strip 3 can still flow into the atomizing assembly through the conductive terminal 2, thereby ensuring normal power supply of the atomizer.

Further, as shown in FIG. 2, the conductive strip 3 is provided with an avoidance groove 32 for receiving the contact portion 21, and the shape of the avoidance groove 32 is fit to the contact portion 21. The avoidance groove 32 may be a groove or a slot, and may have a shape of a circle, an ellipse, a square, a semicircle or the like. In the present embodiment, since the contact portion 21 is of a disc shape, the avoidance groove 32 may also be provided as a circular groove correspondingly. Further, in order to facilitate the mounting and detaching of the conductive terminal 2, the avoidance groove 32 may be also provided as a semicircular slot, and the conductive terminal 2 may be mounted or taken out through one end of the slot opening as a force receiving portion. In the present embodiment, the first through hole 31 is located on the bottom wall of the avoidance groove 32. When the contact portion 21 is placed in the avoidance groove 32, the edge of the contact portion 21 is in contact with the side wall of the avoidance groove 32, so that the contact portion 21 can be limited in position by the avoidance groove 32 to prevent the contact portion 21 from being displaced in the radial direction so as to cause the conductive terminal 2 to shake. At the same time, the connecting portion 22 passes through the first through hole 31 and is electrically connected with the atomizing assembly. Preferably, the depth of the avoidance groove 32 is equal to the thickness of the contact portion 21, so that when the contact portion 21 is placed in the avoidance groove 32, the upper surface of the contact portion 21 and the surface of the conductive strip 3 are located on the same plane to form a contact plane, which increases the area of contact with the output electrode of the power supply end, and facilitates the contact of the output electrode of the external power supply with the two conductive terminals 2 and/or the corresponding conductive strips 3 to form a power supply circuit and power the atomizing assembly. It should be noted that, in actual applications, the conductive strip 3 and the conductive terminal 2 may be connected by other structures. For example, the conductive strip 3 and the two conductive terminals 2 may be integrally formed and directly mounted on the main body 1 so that the atomizer has a large contact plane for making electrical contact with the external power supply.

In the present embodiment, as shown in FIG. 1 and FIG. 2, the main body 1 comprises a base 11 and a housing 12, the base 11 is provided with a receiving groove 111 at one end, and covers the housing 12 at the other end and forms a closed receiving chamber (not shown) with the housing 12. The atomizing assembly is connected with the base 11 and placed in the receiving chamber. The two conductive strips 3 are both placed in the receiving groove 111, and the two conductive strips 3 are separated from each other. Correspondingly, the bottom wall of the receiving groove 111 is provided with a second through hole 113, and the second through hole 113 is concentric with the first through hole 31, so that the connecting portion 22 can be partially placed in the receiving chamber through the first through hole 31 and the second through hole 113 sequentially, and is electrically connected with the atomizing assembly located in the receiving chamber.

Figure 3:
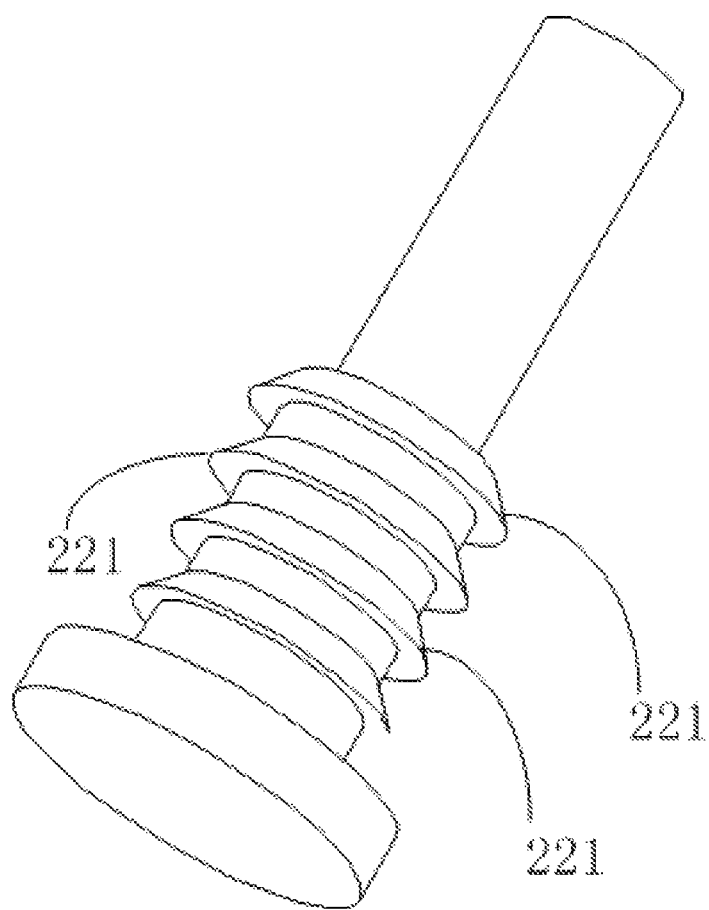
FIG. 3 is a schematic diagram illustrating a first angle of a conductive terminal according to the present invention.
Figure 4:
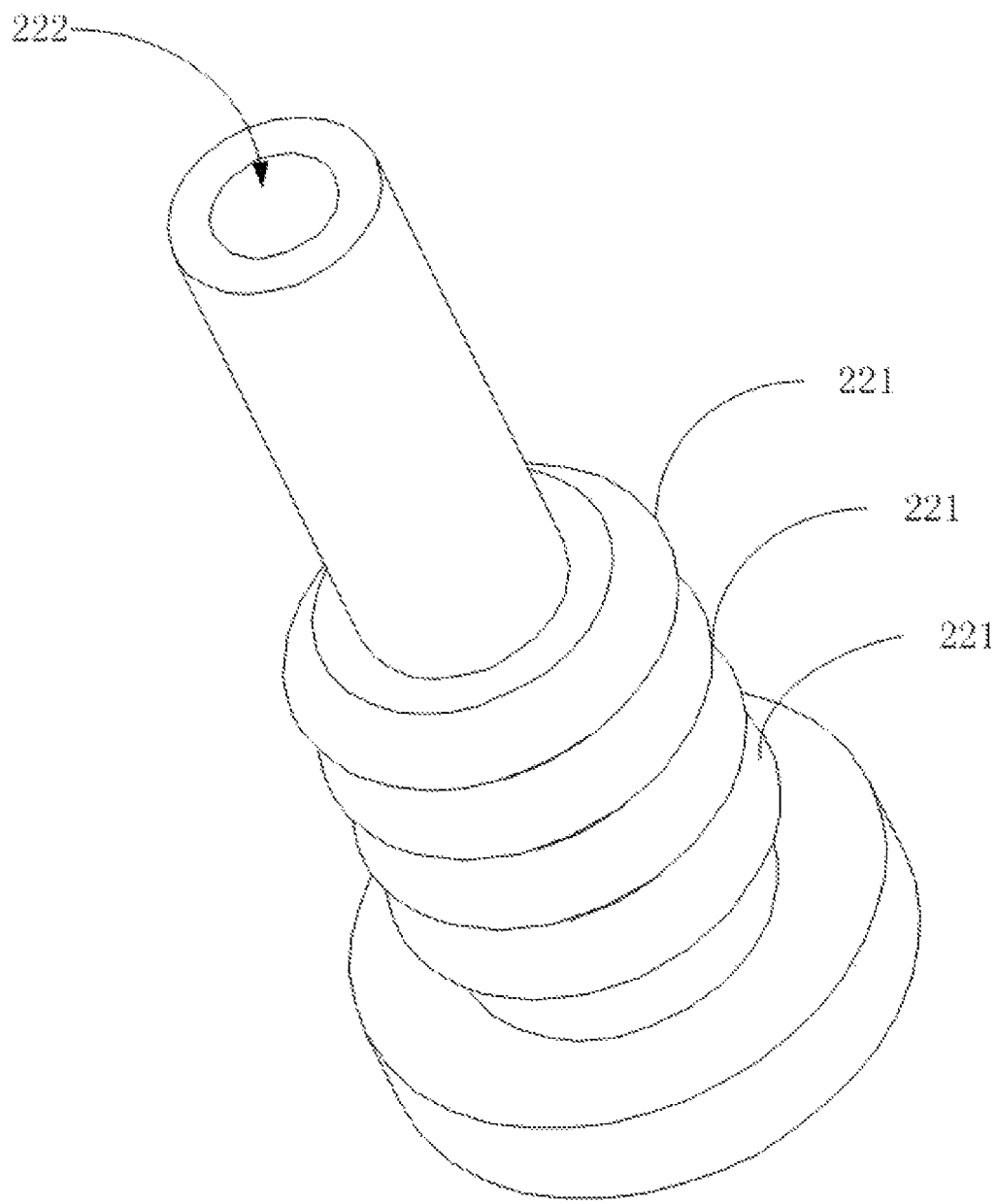
FIG. 4 is a schematic diagram illustrating a second angle of a conductive terminal according to the present invention.

As shown in FIG. 2-4, since the receiving chamber is filled with tobacco tar, in order to prevent the tobacco tar from leaking from the second through hole 113, the outer wall of the connecting portion 22 is provided with at least one oil-sealing rim 221 at intervals circumferentially, and the oil-sealing rim 221 is abutted against the inner wall of the second through hole 113 to form an interference fit, preventing the tobacco tar in the receiving chamber from leaking from the gap between the inner wall of the second through hole 113 and the connecting portion 22. Further, the oil-sealing rim 221 has a truncated cone shape, and the diameter thereof gradually decreases in a direction away from the contact portion 21. That is, the end of the oil-sealing rim 221 near the contact portion 21 is a wide-diameter end, and the end of the oil-sealing rim 221 away from the contact portion 21 is a narrow-diameter end. Thus, when the conductive terminal 2 is sequentially mounted into the first through hole 31 and the second through hole 113 from the end of the connecting portion 22 away from the contact portion 21, the narrow-diameter end of the oil-sealing rim 221 is first in contact with the inner wall of the second through hole 113 and is pressed. As the two conductive terminals 2 continue to penetrate into the second through hole 113, the wide-diameter end of the oil-sealing rim 221 is in contact with the inner wall of the second through hole 113 and is pressed. In this way, the pressing force that the oil-sealing rim 221 is subjected to in the mounting process is gradually increased from being small to being large, so that the gap between the conductive terminal 2 and the second through hole 113 is gradually filled by the oil-sealing rim 221. It is not only advantageous for mounting the conductive terminal 2, but also increases the resistance of taking out the conductive terminal 2 at the same time, preventing the conductive terminal 2 from coming out of the second through hole 113.

It can be understood that, in actual applications, it is not limited to the above manner in which the oil-sealing rims 221 arranged at intervals are provided on the outer periphery of the conductive terminal 2 for sealing. For example, the manner, in which a sealing ring or the like sleeved on the outer periphery of the conductive terminal 2 is abutted against the inner wall of the second through hole for sealing, is also within the scope of protection of the present invention.

In the present embodiment, the atomizing assembly comprises a mounting base 13, an oil guiding core 14, and a heating wire (not shown). The mounting base 13 is connected with one end of the base 11 where the receiving groove 111 is not provided. The mounting base 13 is provided with a mounting groove. The mounting groove and the base 11 enclose an atomizing chamber. Further, the side wall of the mounting groove is provided with two avoidance holes for receiving the oil guiding core 14, and the oil guiding core 14 sequentially passes through the two avoidance holes and is erected on the base 13. A portion of the oil guiding core 14 between the two avoidance holes is placed in the atomizing chamber. The heating wire is wound around a portion of the oil guiding core 14 placed in the atomizing chamber, and both ends are led out from the oil guiding core 14, respectively. One end of the connecting portion 22 of the two conductive terminals 2 away from the contact portion 21 is provided with a socket 222. One end of the heating wire is placed in the socket 222 of the connecting portion 22 of one conductive terminal 2, and is abutted against the inner wall of the socket 222; the other end of the heating wire is placed in the socket 222 of the connecting portion 22 of the other conductive terminal 2, and is abutted against the inner wall of the socket 222, so that a stable connection between the conductive terminal 2 and the heating wire is ensured. Here, in the present embodiment, both ends of the heating wire are engaged in the two sockets 222 through interference fitting, respectively, so as to complete fixing. When the heating wire needs to be replaced, the heating wire is pulled out from the socket 222 without welding, effectively preventing other structures from being burnt due to welding in a small space. At the same time, it is easy for the user to mount and detach.

The receiving groove 111 is further provided with an air inlet 112. The two conductive strips 3 are located at both sides of the air inlet 112, respectively, and are mirror-imaged with the air inlet 112 as the center. That is, an air inlet 112 is provided in the region where the two conductive strips 3 are spaced apart from each other, and the two conductive strips 3 are separated by the air inlet 112 to avoid short-circuiting. Further, the atomizing assembly is provided with an air flow passage communicated with the air inlet 112, and air entering from the air inlet 112 enters the atomizing chamber through the air flow passage to provide oxygen for atomizing. Correspondingly, one end of the housing 12 away from the base 11 is provided with a nozzle, and the nozzle is communicated with the air flow passage and the atomizing chamber, so that the user can inhale the generated smoke through the nozzle.

The present invention further provides an electronic cigarette, comprising a battery assembly and an atomizer as described above, wherein the atomizer is electrically connected with the battery assembly through the two conductive terminals and/or the two conductive strips. Refer to the above embodiment for the specific structure of the atomizer. Due to the use of all the technical solutions of all the above embodiments, the electronic cigarette has at least all the beneficial effects brought by the technical solutions of the above embodiments, which will not be described in detail herein.

The above are preferred embodiments of the present invention merely and are not intended to limit the patent scope of protection of the present invention. Any equivalent structures made according to the description and the accompanying drawings of the present invention without departing from the idea of the present invention, or any equivalent structures applied in other relevant technical fields directly or indirectly are intended to be included in the patent scope of protection of the present invention.

What is claimed is:

1. An atomizer, comprising:
a main body,
wherein the main body is provided with an atomizing assembly and two conductive terminals, the two conductive terminals are electrically connected with the atomizing assembly at one end, and are electrically connected with an external power supply at the other end; the main body is further provided with two conductive strips, and the two conductive strips are electrically connected with the two conductive terminals, respectively, and are both capable of being electrically connected with the external power supply,
wherein the conductive terminal comprises a contact portion and a connecting portion, one end of the connecting portion is connected with the contact portion, the other end is electrically connected with the atomizing assembly the conductive strip is provided with a first through hole and is sleeved at the connecting portion through the first through hole, and is fit to the contact portion.

2. The atomizer according to claim 1, wherein the conductive strip is provided with an avoidance groove, the first through hole is located at the bottom wall of the avoidance groove, the connecting portion passes through the first through hole and is electrically connected with the atomizing assembly, and the contact portion is placed in the avoidance groove.

3. The atomizer according to claim 2, wherein the depth of the avoidance groove is equal to the thickness of the contact portion.

4. The atomizer according to claim 1, wherein the main body comprises a base and a housing, the base is provided with a receiving groove at one end, and covers the housing at the other end and forms a receiving chamber with the housing, the atomizing assembly is connected with the base and placed in the receiving chamber; the bottom wall of the receiving groove is provided with a second through hole concentric with the first through hole, the conductive strip is placed in the receiving groove, and the conductive terminal passes through the first through hole and the second through hole sequentially and is electrically connected with the atomizing assembly.

5. The atomizer according to claim 4, wherein the bottom wall of the receiving groove is further provided with an air inlet, the two conductive strips are located at both sides of the air inlet, respectively, and the atomizing assembly is provided with an air flow passage communicated with the air inlet.

6. The atomizer according to claim 4, wherein the outer wall of the connecting portion is provided with at least one oil-sealing rim at intervals circumferentially, and the oil-sealing rim is abutted against the inner wall of the second through hole.

7. The atomizer according to claim 6, wherein the oil-sealing rim has a truncated cone shape, and the diameter of the oil-sealing rim decreases in a direction away from the contact portion.

8. The atomizer according to claim 1, wherein the atomizing assembly comprises a mounting base, an oil guiding core mounted on the mounting base.

9. An electronic cigarette comprising:
a battery assembly, and
an atomizer comprising:
a main body,
wherein the main body is provided with an atomizing assembly and two conductive terminals, the two conductive terminals are electrically connected with the atomizing assembly at one end, and are electrically connected with an external power supply at the other end; the main body is further provided with two conductive strips, and the two conductive strips are electrically connected with the two conductive terminals, respectively, and are both capable of being electrically connected with the external power supply,
wherein the atomizer is electrically connected with the battery assembly through the conductive terminal and/or the conductive strip,
wherein the conductive terminal comprises a contact portion and a connecting portion, one end of the connecting portion is connected with the contact portion, the other end is electrically connected with the atomizing assembly; the conductive strip is provided with a first through hole and is sleeved at the connecting portion through the first through hole, and is fit to the contact portion.

10. The electronic cigarette according to claim 9, wherein the conductive strip is provided with an avoidance groove, the first through hole is located at the bottom wall of the avoidance groove, the connecting portion passes through the first through hole and is electrically connected with the atomizing assembly, and the contact portion is placed in the avoidance groove.

11. The electronic cigarette according to claim 10, wherein the depth of the avoidance groove is equal to the thickness of the contact portion.

12. The electronic cigarette according to claim 9, wherein the main body comprises a base and a housing, the base is provided with a receiving groove at one end, and covers the housing at the other end and forms a receiving chamber with the housing, the atomizing assembly is connected with the base and placed in the receiving chamber; the bottom wall of the receiving groove is provided with a second through hole concentric with the first through hole, the conductive strip is placed in the receiving groove, and the conductive terminal passes through the first through hole and the second through hole sequentially and is electrically connected with the atomizing assembly.

13. The electronic cigarette according to claim 12, wherein the bottom wall of the receiving groove is further provided with an air inlet, the two conductive strips are located at both sides of the air inlet, respectively, and the atomizing assembly is provided with an air flow passage communicated with the air inlet.

14. The electronic cigarette according to claim 12, wherein the outer wall of the connecting portion is provided with at least one oil-sealing rim at intervals circumferentially, and the oil-sealing rim is abutted against the inner wall of the second through hole.

15. The electronic cigarette according to claim 14, wherein the oil-sealing rim has a truncated cone shape, and the diameter of the oil-sealing rim decreases in a direction away from the contact portion.

16. The electronic cigarette according to claim 9, wherein the atomizing assembly comprises a mounting base, an oil guiding core mounted on the mounting base.

* * * * *